United States Patent
Yamamoto (10) Patent No.: US 8,172,971 B2
(45) Date of Patent: May 8, 2012

(54) JOINING APPARATUS AND METHOD OF MANUFACTURING ABSORBENT ARTICLE

(75) Inventor: Hiroki Yamamoto, Kanonji (JP)

(73) Assignee: Uni-Charm Corporation, Ehime (JP)

( * ) Notice: Subject to any disclaimer, the term of this patent is extended or adjusted under 35 U.S.C. 154(b) by 249 days.

(21) Appl. No.: 12/715,857

(22) Filed: Mar. 2, 2010

(65) Prior Publication Data
US 2010/0218881 A1 Sep. 2, 2010

(30) Foreign Application Priority Data

Mar. 2, 2009 (JP) ................... 2009-048436
Feb. 26, 2010 (JP) ................... 2010-042135

(51) Int. Cl.
*B32B 37/00* (2006.01)

(52) U.S. Cl. .................... 156/73.1; 156/580.2

(58) Field of Classification Search ............... 156/73.1, 156/580.1, 580.2; 264/442, 443, 444, 445; 425/174.2; 228/1.1, 110.1; 310/321, 323.01, 310/323.18

See application file for complete search history.

(56) References Cited

U.S. PATENT DOCUMENTS

| | | | |
|---|---|---|---|
| 4,690,722 A * | 9/1987 | Flood | 156/510 |
| 7,204,899 B2 * | 4/2007 | Van Eperen | 156/73.3 |
| 7,341,084 B2 * | 3/2008 | Van Eperen | 156/510 |

FOREIGN PATENT DOCUMENTS

JP  05-015551 A  1/1993

* cited by examiner

*Primary Examiner* — James Sells
(74) *Attorney, Agent, or Firm* — Lowe, Hauptman, Ham & Berner, LLP (57) ABSTRACT

A joining apparatus includes an ultrasonic vibrating device, and an anvil roller facing the ultrasonic vibrating device with superimposed continua of front waistline portions and back waistline portions interposed therebetween. The anvil roller includes a protrusion configured to press the continua in a predetermined region between the anvil roller and the ultrasonic vibrating device, a motor configured to rotate the anvil roller, a belt configured to connect the anvil roller and the motor and to be driven by the motor, and a pressing mechanism configured to press the belt in a cross direction perpendicular to a driving direction of the belt.

7 Claims, 7 Drawing Sheets

JOINING APPARATUS AND METHOD OF MANUFACTURING ABSORBENT ARTICLE

TECHNICAL FIELD

The present disclosure relates to a joining apparatus for joining two or more superimposed layers, and a method of manufacturing an absorbent article.

BACKGROUND ART

An absorbent article, such as a pants-type disposable diaper, includes: a front waistline portion to be fitted to the front waist of a wearer; a back waistline portion to be fitted to the back waist of the wearer; and a crotch portion to be fitted to the crotch of the wearer. Here, leg-surrounding regions into which the legs of the wearer are inserted are formed at both sides of the crotch portion.

The front waistline portion and the back waistline portion are joined to each other in a region extending from an edge portion of a waist opening to be fit around the body of the wearer to each leg-surrounding region. Japanese Patent Application Publication No. Hei 5-15551 discloses a technique of joining a web in predetermined regions thereof, where joint portions of the front waistline portion and the back waistline portion are to be formed, by causing a joining apparatus to apply ultrasonic vibration to the predetermined regions (for example, see PTL 1).

In general, the joining apparatus includes: an ultrasonic vibrating device applying ultrasonic vibration to the predetermined regions of continua of diaper components under conveyance; an anvil roller including protrusions for pressing the continua in the predetermined regions between the anvil roller and the ultrasonic vibrating device; a motor rotating the anvil roller; and a belt (connector) connecting the anvil roller and the motor.

In the joining apparatus with the aforementioned configuration, the driving of the motor in association with the conveyance of the continua rotates the anvil roller via the belt. Then, an ultrasonic horn provided in the ultrasonic vibrating device and one of the protrusions of the anvil roller work together to nip the continua in each predetermined region at a certain interval (i.e., the interval corresponding to a distance between each adjacent predetermined regions). Thereby, the continua in the predetermined region are subjected to ultrasonic vibration and joined.

The inventors have discovered that, in the known joining apparatus mentioned above, while the motor keeps driving the belt to rotate the anvil roller, the rotational speed of the anvil roller is reduced temporarily when the ultrasonic horn of the ultrasonic vibrating device comes in contact with each protrusion of the anvil roller. This induces a problem of loosening the belt between the motor and the anvil roller, and thus causing the belt to run off the anvil roller or the motor.

Moreover, the rotational speed of the anvil roller is changed drastically when the ultrasonic horn comes in contact with the protrusion. This results in a non-uniform joining in the predetermined regions, that is, a non-uniform joining in the joint portions of the front waistline portion and the back waistline portion.

It is desirable to provide a joining apparatus and a method of manufacturing absorbent articles which are capable of achieving a more uniform joining in predetermined regions thereof, where joint portions of a front waistline portion and a back waistline portion are to be formed, and of reliably preventing a connector such as a belt from running off an anvil roller or a motor, in a case where the anvil roller and the motor are connected to each other via the connector.

CITATION LIST

Patent Literature

PTL 1. Japanese Patent Application Publication No. Hei 5-15551 (pages 2 and 3, and FIG. 4)

SUMMARY

To solve the above-described problem, the present invention has the following aspects. An aspect of the present invention provides a joining apparatus which is used for manufacturing an absorbent article and which joins a continuum of front waistline portions and a continuum of back waistline portions in a predetermined region, where a joint portion of each of the front waistline portions and each of the back waistline portions is to be formed, after the continuum of the front waistline portions and the continuum of the back waistline portions continuously fed are superimposed, the continua being prepared to form an absorbent article. The joining apparatus includes an ultrasonic vibrating device configured to apply ultrasonic vibration to the predetermined region, an anvil roller facing the ultrasonic vibrating device with the superimposed continua of the front waistline portions and the back waistline portions interposed therebetween, and including a protrusion configured to press the continua in the predetermined region between the anvil roller and the ultrasonic vibrating device, a motor configured to rotate the anvil roller, a connector configured to connect the anvil roller and the motor and to be driven by the motor, and a pressing mechanism configured to press the connector in a cross direction perpendicular to a driving direction of the connector.

The aspect of the present invention can provide a joining apparatus and a method of manufacturing an absorbent article which are capable of achieving a more uniform joining in predetermined regions thereof, where joint portions of a front waistline portion and a back waistline portion are to be formed, and of reliably preventing a connector such as a belt from running off an anvil roller or a motor, in a case where the anvil roller and the motor are connected to each other via the connector.

BRIEF DESCRIPTION OF DRAWINGS

Parts (a) and (b) of FIG. 6 are schematic views of an anvil-side pulley and the pressing mechanisms in different positions according to one or more embodiments.

DETAILED DESCRIPTION

Hereinafter, a joining apparatus and a method of manufacturing absorbent articles according to one or more embodiments of the present invention will be described with reference to the accompanying drawings. Note that, in the following description of the drawings, same or similar reference signs denote same or similar elements and portions. In addition, it should be noted that the drawings are schematic and are not to scale unless otherwise specified.

Therefore, specific dimensions and the like should be determined in consideration of the following description. Moreover, the drawings do not necessarily reflect the real-life dimensional relationships and ratios of components.

Firstly, a configuration of an absorbent article 1 according to one or more embodiments will be explained with reference to FIG. 1 which is a partially cutaway perspective of the absorbent article 1. In this particularly illustrated embodiment, the absorbent article 1 is a disposable pants-type diaper for adults.

Figure 1:
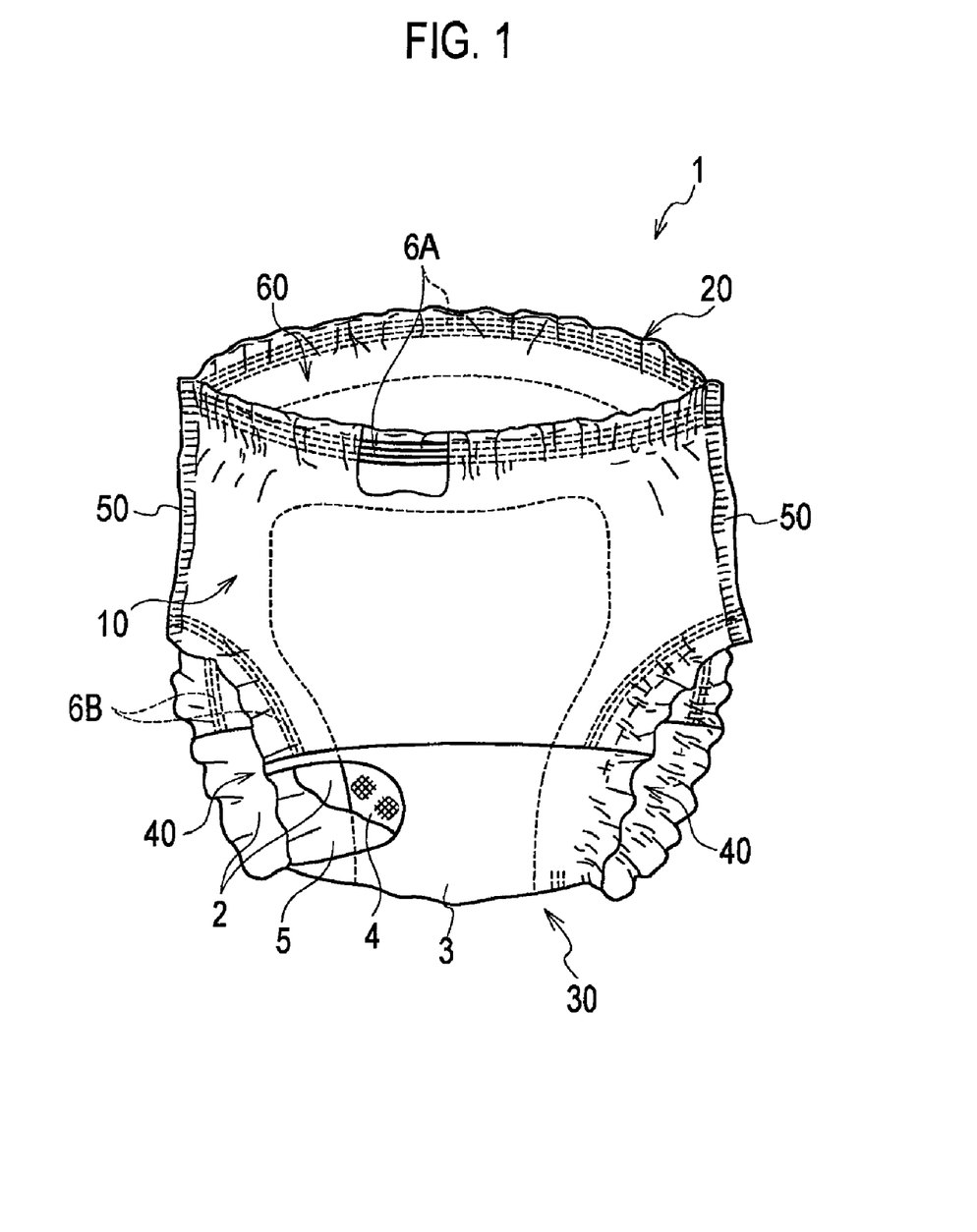
FIG. 1 is a partially cutaway, perspective view of an absorbent article according to one or more embodiments.

As shown in FIG. 1, the absorbent article 1 mainly includes a top sheet 2, a back sheet 3, an absorber 4 and a waterproof sheet 5.

The top sheet 2 is adapted to come into contact with the skin of a person to wear the absorbent article 1 (hereinafter, "wearer"). The top sheet 2 is made of a liquid permeable sheet such as a nonwoven fabric or perforated plastic film. The back sheet 3 is provided outside the top sheet 2 (on a side facing away from the wearer). The back sheet 3 is made of a nonwoven fabric or the like.

The absorber 4 is provided between the top sheet 2 and the back sheet 3, for absorbing excretion discharged from the wearer. The absorber 4 is made of a mixture of ground pulp and superabsorbent polymer particles, or the like. The waterproof sheet 5 is provided between the back sheet 3 and the absorber 4, for blocking the permeation of the excretion from the wearer to the outside of the absorbent article 1. The waterproof sheet 5 is made of a liquid impermeable sheet.

The absorbent article 1 thus configured includes, in combination, a front waistline portion 10 to be fitted to the front waist of a wearer, a back waistline portion 20 to be fitted to the back waist of the wearer, and a crotch portion 30 to be fitted to the crotch of the wearer. Incidentally, leg-surrounding openings 40 into which the legs of the wearer are inserted are formed at both sides of the crotch portion 30.

The front waistline portion 10 and the back waistline portion 20 are joined together by joint portions 50, and thereby form a waist opening 60 to be fit around the body of the wearer. A waist gather 6A made of a stretchable rubber strand or the like is provided to an entire peripheral edge of the front waistline portion 10 and the back waistline portion 20.

For example, to make the front waistline portion 10 and the back waistline portion 20 stretchable in the cross direction perpendicular to the front-to-back direction from the front waistline portion 10 toward the back waistline portion 20, the front waistline portion 10 and the back waistline portion 20 may be provided with the waist gather 6A, or may themselves be made of a stretchable sheet.

The crotch portion 30 is provided between the front waistline portion 10 and the back waistline portion 20. Leg gathers 6B made of stretchable rubber strands or the like are provided on both sides of the crotch portion.

For example, to make the crotch portion 30 stretchable in the leg-encircling direction of the absorbent article 1, the crotch portion 30 may be provided with the leg gathers 6B, or may itself be made of a stretchable sheet.

Secondly, a method of manufacturing absorbent articles according to one or more embodiments will be explained with reference to FIG. 2 which is a diagram for explaining a relevant part of the absorbent article manufacturing method.

Figure 2:
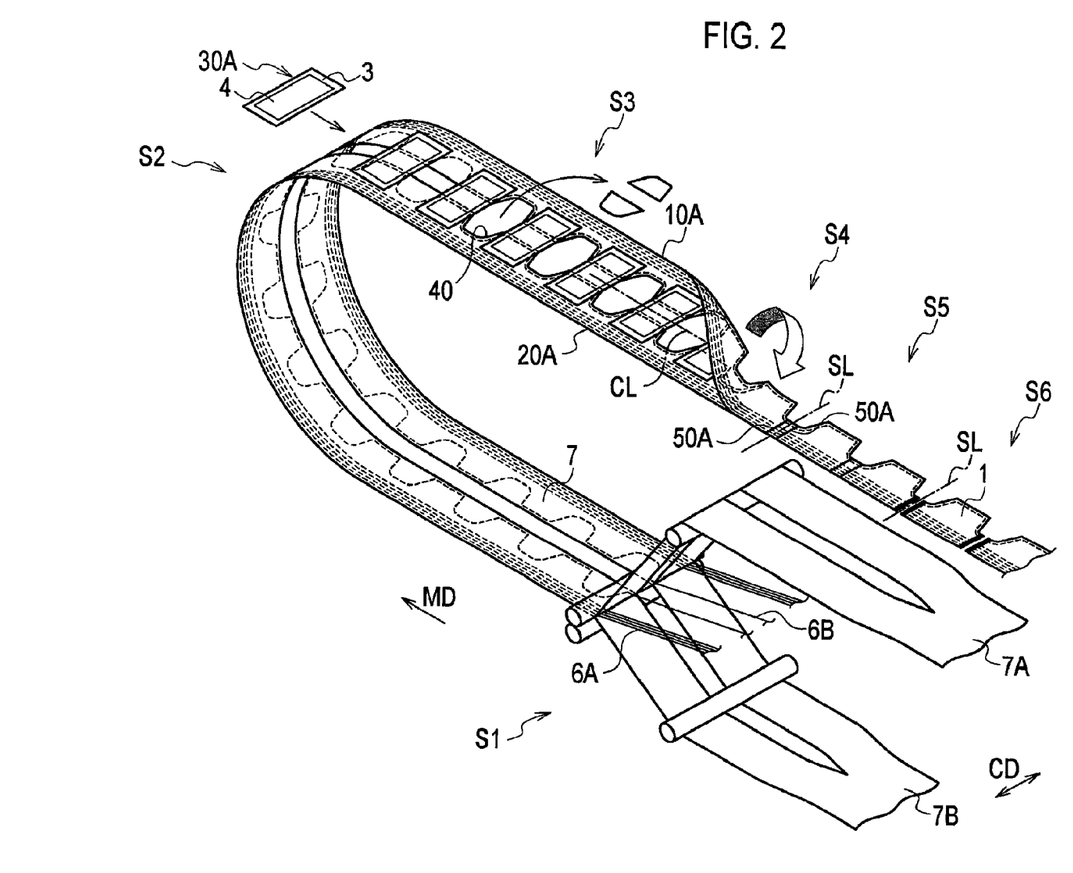
FIG. 2 is a diagram for explaining a relevant part of a method of manufacturing absorbent articles according to one or more embodiments.

As shown in FIG. 2, the method of manufacturing absorbent articles includes at least a waistline forming step S1, an absorber transferring step S2, a leg-surrounding opening forming step S3, a folding step S4, a joining step S5 and a cutting step S6.

In the waistline forming step S1, gathers (a waist gather 6A and/or a leg gather 6B) are placed between a web 7A and a web 7B, and thereby a web 7 prepared to form the front waistline portion 10 and the back waistline portion 20 is formed.

Note that the web 7 (webs 7A, 7B) during conveyance is stretchable in a cross direction CD (width direction) perpendicular to a conveyance direction MD (machine direction) of the web 7. In addition, the web 7 is asymmetrical with respect to a center line CL that bisects a width in the cross direction CD of the web 7 and extends in the conveyance direction MD of the web 7.

In the absorber transferring step S2, a crotch portion member 30A to form the crotch portion 30 is transferred onto the web 7, more specifically, between the front waistline portion 10 and the back waistline portion 20 after the waistline forming step S1. Here, the crotch portion member 30A includes the back sheet 3 and the absorber 4.

In the leg-surrounding opening forming step S3, the leg-surrounding openings 40 (so-called leg holes) are formed by cutting the web 7 (webs 7A, 7B) after the absorber transferring step S2. Here, the formation of the leg-surrounding opening 40 does not necessarily involve cutting only the web 7A and the web 7B, but may involve cutting, together with the web 7A and the web 7B, the back sheet 3 constituting the crotch portion member 30A.

Note that the absorber transferring step S2 and the leg-surrounding forming step S3 may be performed in the reverse order.

In the folding step S4, the web 7 is folded into two parts along a folding line extending in the conveyance direction MD of the web 7 by bringing a side edge 10A of the front waistline portion 10 toward a side edge 20A of the back waistline portion 20, after the leg-surrounding opening forming step S3.

Note that, in this particularly illustrated embodiment, the folding line is the center line CL. However, the folding line is not necessarily the center line CL, and may be shifted from the center line CL toward either of the first side edge 10A and the second side edge 20A.

In the joining step S5, a joining apparatus 100 to be described later applies ultrasonic treatment after the folding step S4 to predetermined regions 50A of the folded web 7, that is, to the predetermined regions 50A where the joint portions 50 of the front waistline portion 10 and the back waistline portion 20 are to be formed. Thereby, the web 7 in the predetermined regions 50A is joined. The predetermined region 50A extends, in the conveyance direction MD, across an imaginary line SL that extends in the cross direction CD and represents a to-be-cut line of the web 7.

In the cutting step S6, the web 7 joined in the predetermined regions 50A is cut along the imaginary lines SL after the joining step S5. Thereby, the absorbent article 1 is manufactured.

Figure 3:
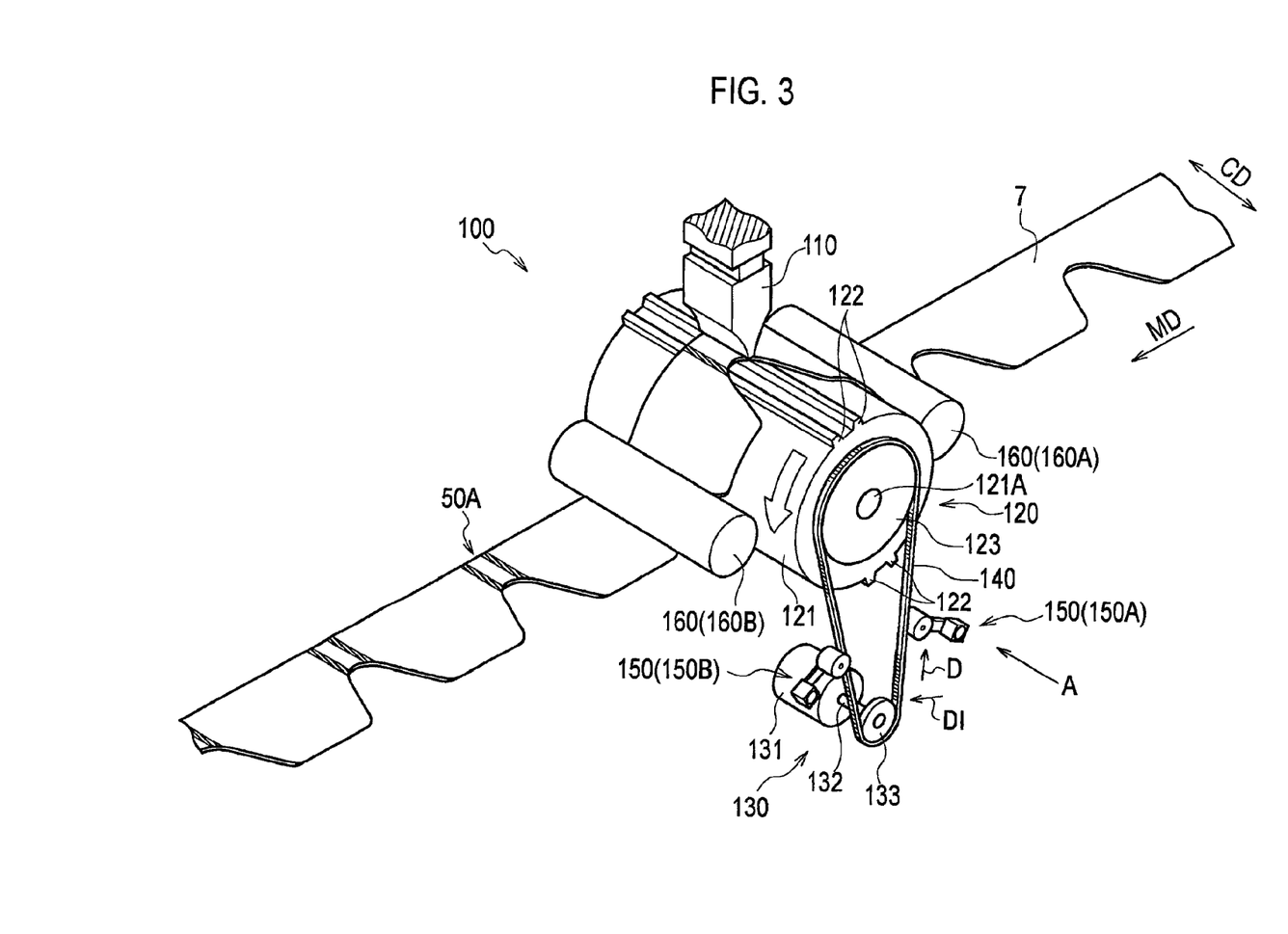
FIG. 3 is a perspective view of a joining apparatus according to one or more embodiments.
Figure 4:
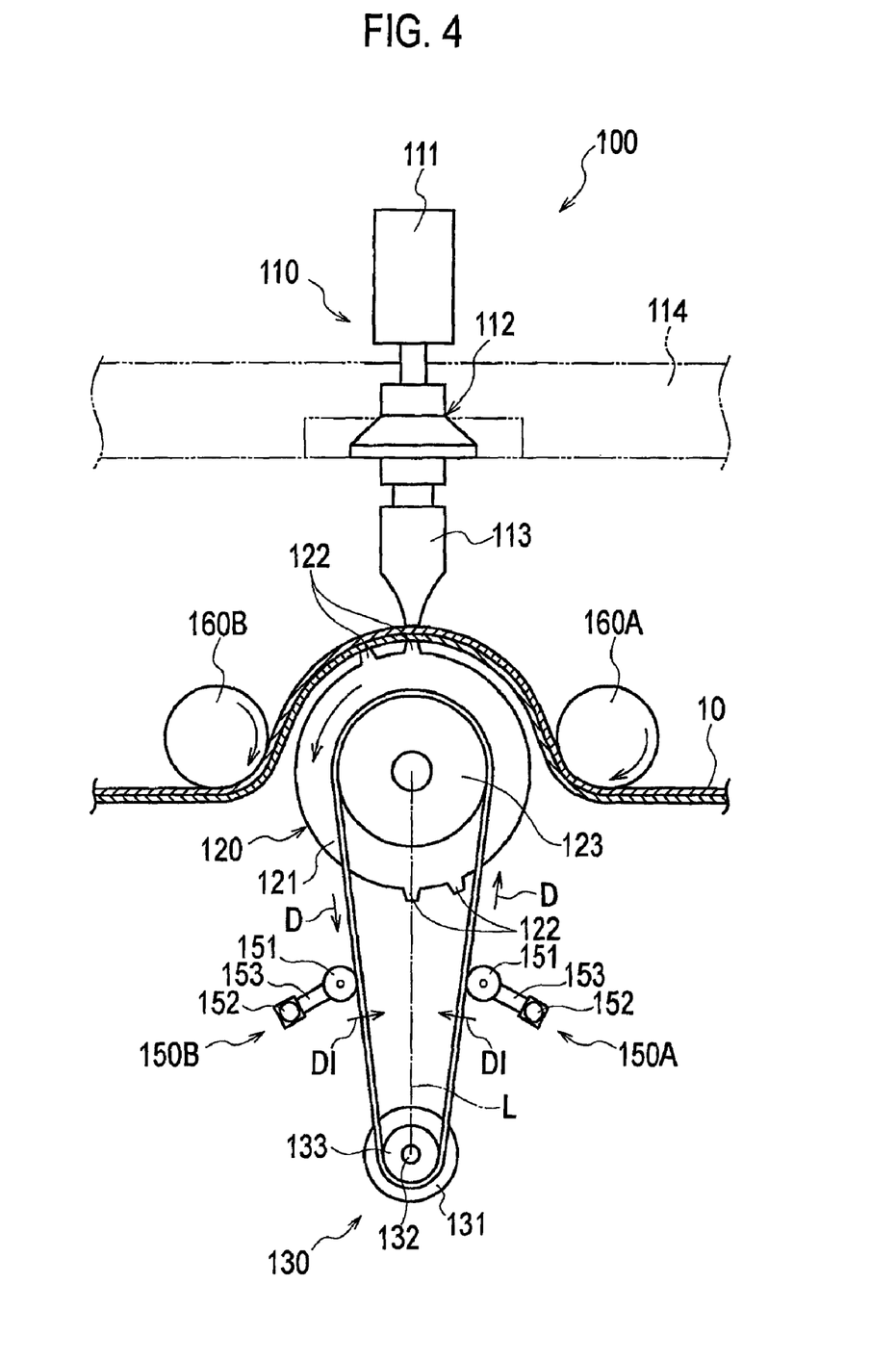
FIG. 4 is a side view of the joining apparatus of FIG. 3.
Figure 5:
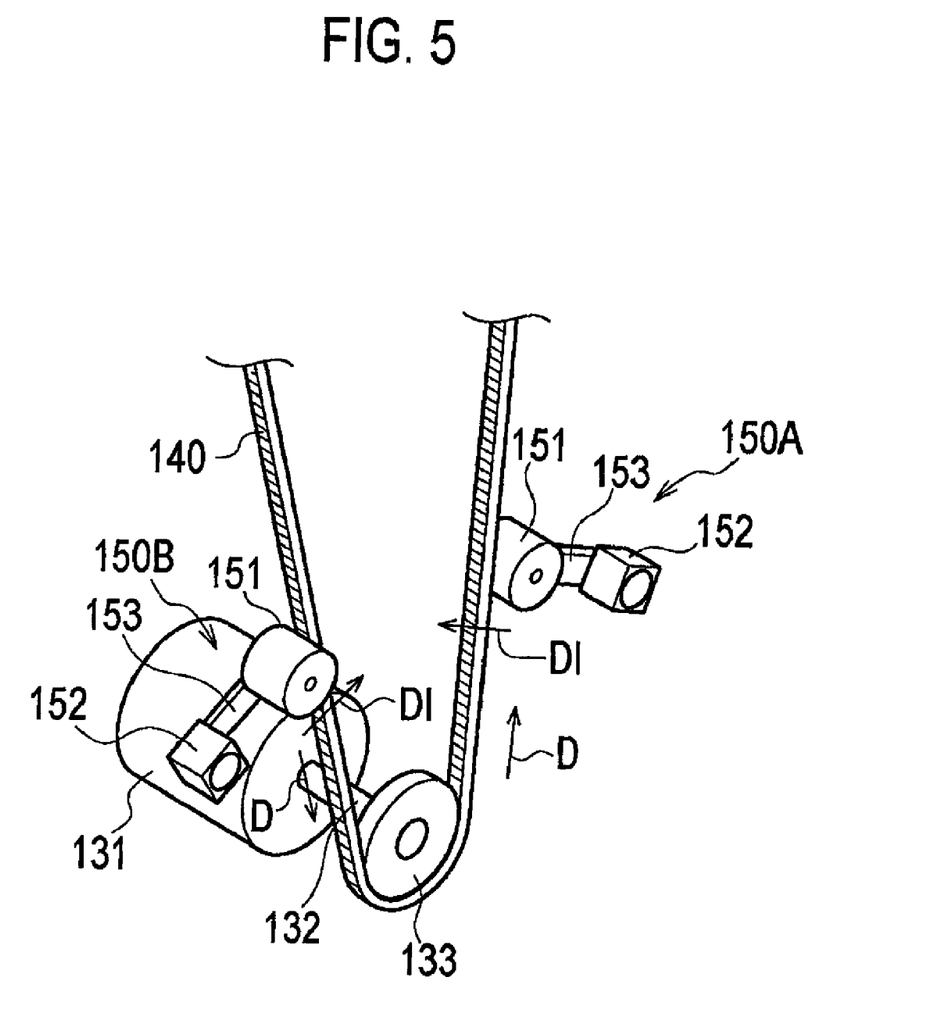
FIG. 5 is an enlarged perspective view of pressing mechanisms according to one or more embodiments.

Next, a configuration of the joining apparatus 100 used in the joining step S5 described above will be explained with reference to FIGS. 3-5. FIG. 3 is a perspective view of the joining apparatus 100 according to one or more embodiments. FIG. 4 is a side view (as seen in the direction of an arrow A of FIG. 3) of the joining apparatus 100 of FIG. 3. FIG. 5 is an enlarged perspective view of pressing mechanisms 150 according to one or more embodiments.

As shown in FIGS. 3 to 5, the joining apparatus 100 is used for manufacturing the absorbent article 1, and joins a continuum of the front waistline portions 10 and a continuum of the back waistline portions 20 in the predetermined regions 50A, where the joint portions 50 of the front waistline portion 10 and the back waistline portion 20 are to be formed, after these continua continuously fed are superimposed. Hereinafter, the continuum of the front waistline portions 10 and the continuum of the back waistline portions 20 are collectively and simply called the "web 7."

To be more specific, the joining apparatus 100 includes an ultrasonic vibrating device 110, an anvil roller 120, a motor 130, a belt 140 (connector), the pressing mechanisms 150 and guide rollers 160.

The ultrasonic vibrating device 110 works with one of protrusions 122 of the anvil roller 120 to be described later to nip the web 7 in each predetermined region 50A, and thus applies ultrasonic vibration to the predetermined region 50A. The ultrasonic vibrating device 110 includes an ultrasonic vibrator 111, a booster 112 and an ultrasonic horn 113.

The ultrasonic vibrator 111 provides ultrasonic vibration to the ultrasonic horn 113 via the booster 112. Here, the ultrasonic vibrator 111 is connected to the booster 112.

The booster 112 amplifies the ultrasonic vibration provided by the ultrasonic vibrator 111. The booster 112 is fixed to a pressurizing arm 114 which adjusts the height of the ultrasonic horn 113. The booster 112 transmits the amplified ultrasonic vibration to the ultrasonic horn 113.

The ultrasonic horn 113 presses the web 7 in each predetermined region 50A against the anvil roller 120, and applies the ultrasonic vibration to the predetermined region 50A. In other words, the ultrasonic horn 113 works with one of the protrusions 122 of the anvil roller 120 to nip the web 7 in each predetermined region 50A. The ultrasonic horn 113 is connected to the pressurizing arm 114 via the booster 112.

The anvil roller 120 conveys the web 7 in the conveyance direction MD while supporting the web 7. The anvil roller 120 faces the ultrasonic vibrating device 110 with the web 7 interposed therebetween. The anvil roller 120 includes an anvil main body 121 and the protrusions 122.

The anvil main body 121 is in the form of a cylinder, and rotates about its central shaft 121A in the conveyance direction MD. On one end face of the anvil main body 121, an anvil-side pulley 123 is provided which is fixed to the central shaft 121A and around which the belt 140 is trained. Thus, the anvil-side pulley 123 rotates at the same speed as the anvil main body 121.

Each protrusion 122 protrudes from the anvil main body 121 outward in the radial direction of the anvil main body 121. The protrusion 122 presses the web 7 in each predetermined region 50A against the ultrasonic vibrating device 110 (ultrasonic horn 113). In other words, in each predetermined region 50A, the protrusion 122 works with the ultrasonic vibrating device 110 to nip the web 7.

The motor 130 rotates the anvil roller 120. The motor 130 is arranged at the anvil roller 120 side of the web 7 (under the anvil roller 120 in the drawings), and is arranged farther from the web 7 than the anvil roller 120. The motor 130 includes a motor main body 131 and a rotational shaft 132. The motor main body 131 includes: a rotor (not shown) rotating about its axis; a stator (not shown) working with the rotor to generate torque; and a bearing (not shown) supporting the rotational shaft 132.

The rotational shaft 132 transmits the rotation of the rotor to the outside, i.e., to the belt 140. On one end of the rotational shaft 132, a motor-side pulley 133 is provided which is fixed to the rotational shaft 132 and around which the belt 140 is trained. Thus, the motor-side pulley 133 rotates at the same speed as the rotational shaft 132 by the rotation of the rotational shaft 132.

The belt 140 is an endless belt. The belt 140 connects the anvil roller 120 (anvil-side pulley 123) and the motor 130 (motor-side pulley 133), and is driven by the motor 130. Thereby, the belt 140 can transmit the rotation of the motor 130 to the anvil roller 120.

The pressing mechanisms 150 constantly press the belt 140 in respective directions transverse to a driving direction D of the belt 140, e.g., in cross directions DI each perpendicular to the driving direction D of the belt 140. When seen in the axial direction of the anvil roller 120 (see FIG. 4), the pressing mechanisms 150 each press the belt 140 toward an imaginary line L connecting the center of the central shaft 121A of the anvil roller 120 and the center of the rotational shaft 132 of the motor 130. In other words, the pressing mechanisms 150 press the belt 140 inward from the outer side of the belt 140.

The pressing mechanisms 150 include a first pressing mechanism 150A and a second pressing mechanism 150B. The first pressing mechanism 150A is arranged to abut on the belt 140 in a region where the belt 140 moves from the motor 130 to the anvil roller 120 in the driving direction D. The second pressing mechanism 150B is arranged to abut on the belt 140 in a region where the belt 140 moves from the anvil roller 120 to the motor 130 in the driving direction D.

The pressing mechanisms 150 (first and second pressing mechanisms 150A and 150B) each include a rotating portion 151, a moving portion 152 and an arm 153. The rotating portion 151 abuts on the belt 140, and is rotated with the rotation of the belt 140 about a shaft (unnumbered) provided to the arm 153. The rotating portion 151 is connected to the moving portion 152 with the arm 153 interposed therebetween. The moving portion 152 is a general suspension unit which moves (for example, biases) the rotating portion 151 in the corresponding cross direction DI. The rotating portion 151 and the arm 153 rotate about the moving portion 152.

The pressing mechanism 150 (the first and second pressing mechanism 150A and 150B) presses such that the belt 140 is located closer to the imaginary line L than a tangent line common to the anvil-side pulley 123 and the motor-side pulley 133.

The guide rollers 160 support the web 7, and change the conveyance direction MD of the web 7. The guide rollers 160 include a first guide roller 160A and a second guide roller 160B. The first guide roller 160A guides the web 7 between the anvil roller 120 and the ultrasonic horn 113. The second guide roller 160B guides part of the web 7, the predetermined region 50A of which has been subjected to ultrasonic vibration, to the next process.

Hereinafter, an operation of the joining apparatus 100 according to one or more embodiments will be briefly described with reference to FIGS. 3 to 6. Parts (a) and (b) of FIG. 6 are schematic views of the anvil roller 120 and the pressing mechanisms 150 in different positions according to one or more embodiments.

As shown in FIGS. 3 to 6, in the joining apparatus 100, the anvil roller 120 rotates in association with the conveyance of the web 7. To put it differently, the driving of the motor 130 rotates the anvil roller 120 via the belt 140. In this event, the rotating portion 151 of each pressing mechanism 150 is moved (biased) by the corresponding moving portion 152 in the corresponding cross direction DI, and thereby presses the belt 140 in the cross direction DI. Hereinafter, an operation of the first and second pressing mechanisms 150A and 150B will be briefly described.

Figure 6:
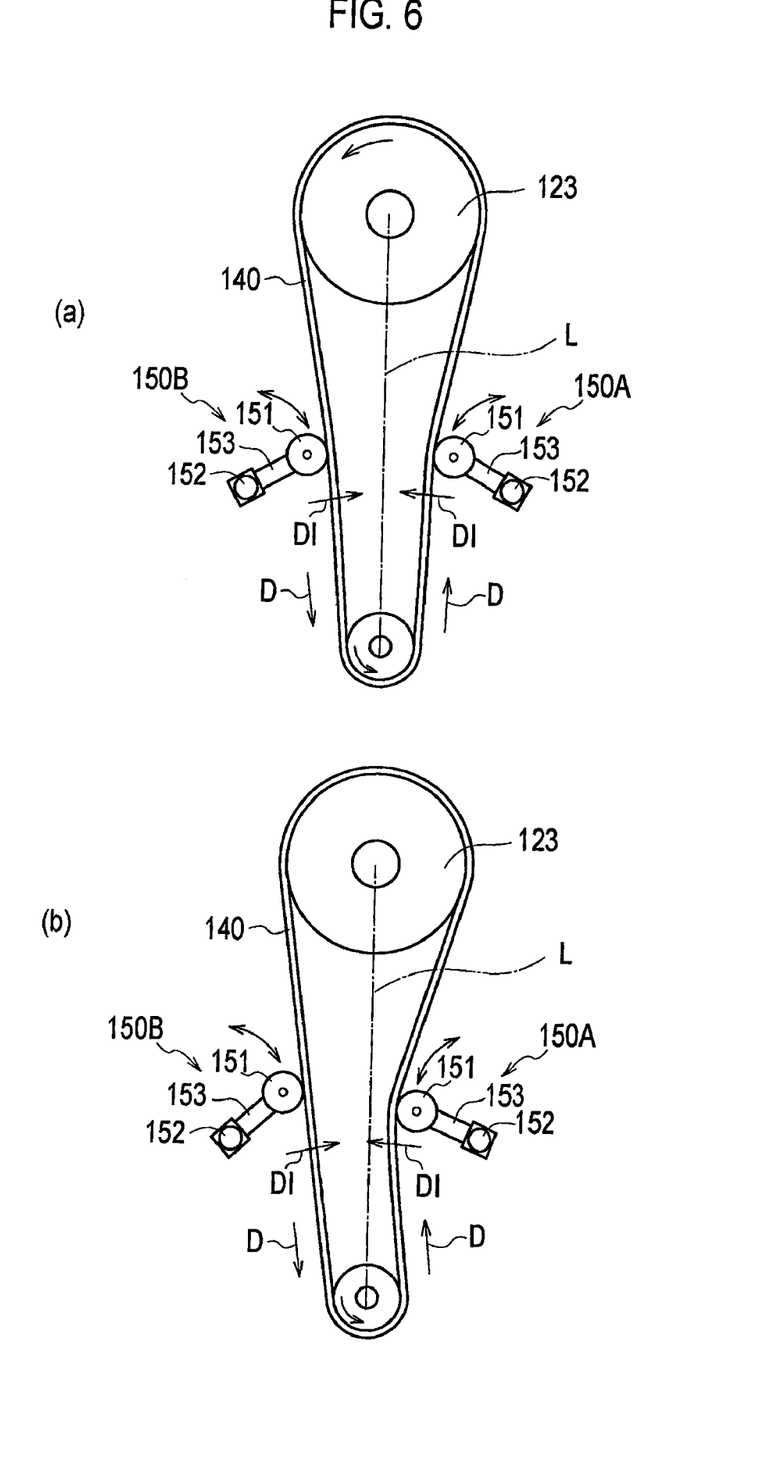

Firstly, on the one hand, the contact between the ultrasonic horn 113 and each protrusion 122 with the web 7 interposed therebetween loosens the belt 140 in a portion where the belt 140 moves from the motor 130 to the anvil roller 120 in the driving direction D (see part (b) of FIG. 6). In this state, the rotating portion 151 of the first pressing mechanism 150A is moved closer to the imaginary line L than in a normal state where the ultrasonic horn 113 and the protrusion 122 are not in contact with each other (see part (a) of FIG. 6). Accordingly, the first pressing mechanism 150A presses the belt 140 toward the imaginary line L, and is thus capable of keeping constant the tension of the belt 140.

Further, the release of the contact between the ultrasonic horn 113 and the protrusion 122 tightens the belt 140 in the portion where the belt 140 moves from the motor 130 to the anvil roller 120 in the driving direction D (see part (a) of FIG. 6). In this state, the rotating portion 151 of the first pressing mechanism 150A is moved farther from the imaginary line L than in the state where the ultrasonic horn 113 and the protrusion 122 are in contact with each other (see part (b) of FIG. 6). Accordingly, the first pressing mechanism 150A returns to a state prior to the pressing of the belt 140. The first pressing mechanism 150A moves into a state that it is attached to the belt 140.

On the other hand, the contact between the ultrasonic horn 113 and the protrusion 122 tightens the belt 140 in a portion where the belt 140 moves from the anvil roller 120 to the motor 130 in the driving direction D (see part (b) of FIG. 6). In this state, the rotating portion 151 of the second pressing mechanism 150B is moved farther from the imaginary line L than in the normal state (see part (a) of FIG. 6). Accordingly, the second pressing mechanism 150B is in a state prior to the pressing of the belt 140. The second pressing mechanism 150B moves into a state that it is attached to the belt 140.

Further, the release of the contact between the ultrasonic horn 113 and the protrusion 122 loosens the belt 140 in the portion where the belt 140 moves from the anvil roller 120 to the motor 130 in the driving direction D (see part (a) of FIG. 6). In this state, the rotating portion 151 of the second pressing mechanism 150B is moved closer to the imaginary line L than the state where the ultrasonic horn 113 and the protrusion 122 are in contact with each other (see part (b) of FIG. 6). Accordingly, the second pressing mechanism 150B presses the belt 140 toward the imaginary line L, and is thus capable of keeping constant the tension of the belt 140.

In the above configuration, the ultrasonic horn 113 and one of the protrusions 122 work together to nip the web 7 in each predetermined region 50A at a certain interval (i.e., the interval corresponding to a distance between each adjacent predetermined regions 50A). Thereby, the ultrasonic horn 113 applies ultrasonic vibration generated by the ultrasonic vibrator 111 to the predetermined region 50A. In this manner, the web 7 in the predetermined regions 50A, where the joint portions 50 of the front waistline portion 10 and the back waistline portion 20 are to be formed, is subjected to ultrasonic vibration and joined.

In the joining apparatus 100 and the method of manufacturing absorbent articles according to the embodiment (s) having been described thus far, the pressing mechanisms 150 press the belt 140 in the respective cross directions DI each perpendicular to the driving direction D of the belt 140. This prevents the belt 140 from being loosened between the motor 130 and the anvil roller 120 when the ultrasonic horn 113 comes in contact with each protrusion 122 and, thereby, preventing the rotational speed of the anvil roller 120 from being temporarily reduced when the horn-protrusion contact occurs. Moreover, this prevents the rotational speed of the anvil roller 120 from being changed drastically when the ultrasonic horn 113 comes in contact with the protrusion 122. These effects make it possible to keep the belt 140 tensioned.

Therefore, it is possible to keep the belt 140 being tensioned, to join the predetermined regions 50A in the conveyance direction of the web 7 at a certain interval, and to surly prevent the belt 140 from running off the anvil roller 120 and the motor 130.

The inventors are aware of a known technique in which a shaft (similar to shaft 121A) coupled to the anvil-side pulley 123 is provided with a rubber material interposed between the shaft and the anvil-side pulley 123, in order to cushion the impact of the contact between the ultrasonic horn 113 and each protrusion 122 and to prevent, if at all possible, the belt 140 from running off the anvil roller 120 or the motor 130. However, this technique is not suited to finely control the torque of the anvil roller 120. To cope with this, the anvil roller 120 is rotated via the belt 140 in this embodiment. Accordingly, the torque of the anvil roller 120 can be finely controlled.

In the joining apparatus 100 and the method of manufacturing absorbent articles according to the disclosed embodiment(s), the pressing mechanisms 150 constantly press the belt 140 from the first pressing mechanism 150A and/or the second pressing mechanism 150B. In other words, each moving portion 152 constantly biases the corresponding rotating portion 151 in the corresponding cross direction DI. Accordingly, the pressing mechanisms 150 constantly press the belt 140 in the respective cross directions DI regardless of whether the rotation of the anvil roller 120 is reduced. This arrangement makes it possible to keep the belt 140 tensioned and to more reliably prevent the belt 140 from running off the anvil roller 120 or the motor 130.

In the joining apparatus 100 and the method of manufacturing absorbent articles according to the disclosed embodiment (s), the pressing mechanisms 150 are arranged to abut on the belt 140 in the region where the belt 140 moves from the motor 130 to the anvil roller 120 in the driving direction D and the region where the belt 140 moves from the anvil roller 120 to the motor 130 in the driving direction D, respectively. With this arrangement, the pressing mechanisms 150 press the belt 140 in the respective cross directions DI in these regions where the belt 140 is likely to be loosened. As a result, the belt 140 can be kept tensioned reliably.

In the joining apparatus 100 and the method of manufacturing absorbent articles according to the disclosed embodiment (s), the pressing mechanisms 150 each press the belt 140 toward the imaginary line L, as seen in the axial direction of the anvil roller 120 (see FIG. 4). In other words, the pressing mechanisms 150 press the belt 140 inward from the outer side of the belt 140. Such a way of pressing the belt 140 makes the belt 140 more likely to be trained around the anvil-side pulley 123 or the motor-side pulley 133 than a way in which the pressing mechanisms 150 press the belt 140 outward from the inner side of the belt 140. Thus, the belt 140 can be more reliably prevented from running off the anvil roller 120 or the motor 130.

In the joining apparatus 100 and the method of manufacturing absorbent articles according to the disclosed embodiment(s), the pressing mechanisms 150 include the first pressing mechanism 150A and the second pressing mechanism 150B. This enables the belt 140 to rotate while the looseness of the belt 140 is more suppressed on each of the first pressing mechanism 150A side and the second pressing mechanism 150B side, than a case where only one of the first and second pressing mechanisms 150A and 150B is arranged. This arrangement reduces the looseness degree of the belt 140, i.e., how much the belt 140 is loosened. As a result, the belt 140 can be more reliably prevented from running off the anvil roller 120 or the motor 130.

Note that, both of the first and second pressing mechanisms 150A and 150B are not necessarily provided. For example, only one of the first and second pressing mechanisms 150A and 150B may be provided instead. In this case, it is particularly preferable to choose the second pressing mechanism 150B with which the belt 140 is more likely to be kept tensioned. It is however within the scope of the invention to provide only the first pressing mechanism 150B.

Thus, one or more of the aspects disclosed above can provide a joining apparatus and a method of manufacturing absorbent articles which are capable of achieving a more uniform joining in predetermined regions, where joint portions of a front waistline portion and a back waistline portion are to be formed, and reliably preventing a connector, such as a belt, from running off an anvil roller or a motor, where the anvil roller and the motor are connected to each other via the connector.

Modified Examples

Figure 7:
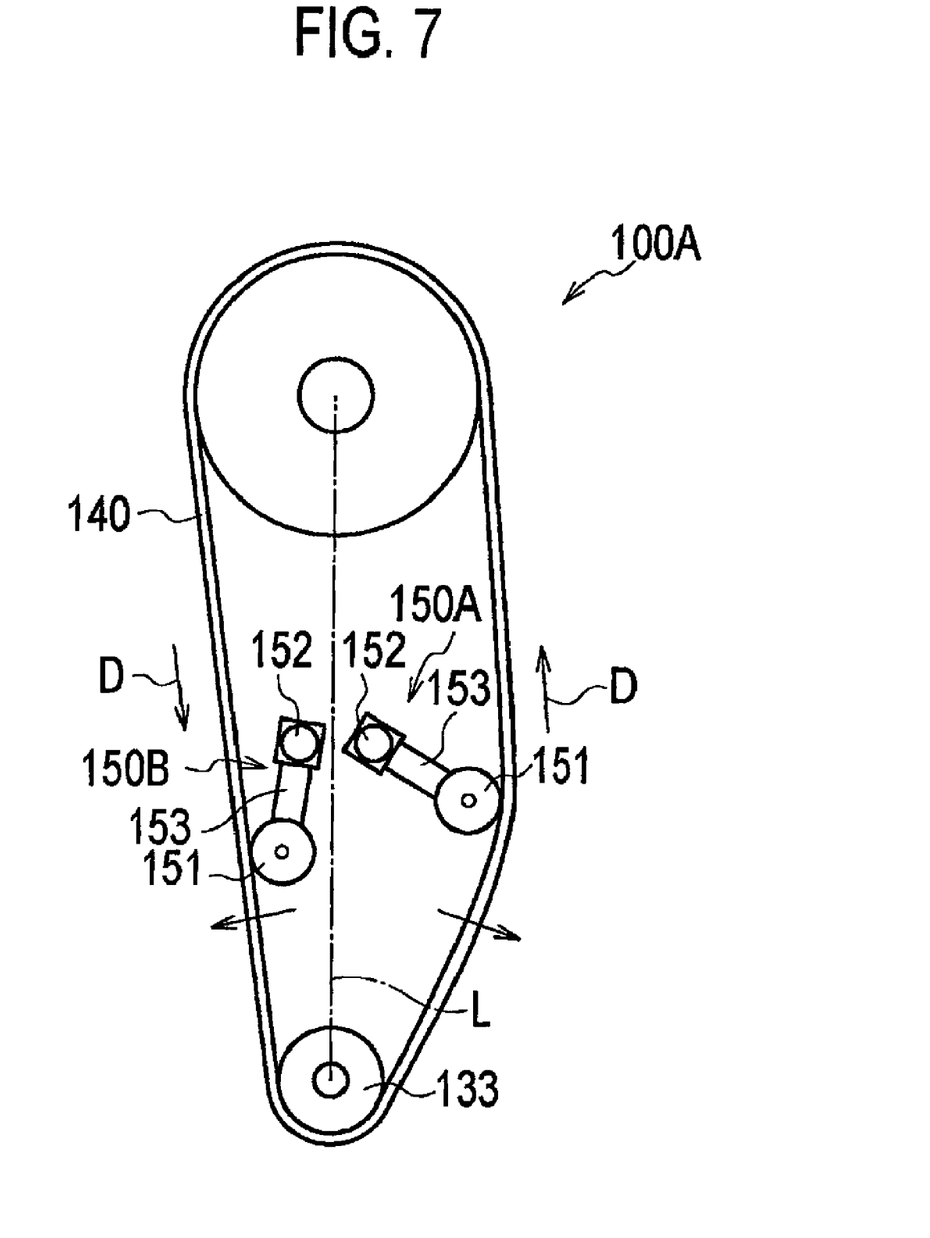
FIG. 7 is a schematic view of an anvil roller and pressing mechanisms of a joining apparatus according to a modified example.

The joining apparatus 100 according to the foregoing description may be modified in the following manner. FIG. 7 is a schematic view of an anvil roller 120 and pressing mechanisms 150 of a joining apparatus 100A according to a modified example. Here, description will be provided mainly for differences from the foregoing description, with the same or similar reference signs denoting the same or similar elements.

In the joining apparatus 100 according to the foregoing description, the pressing mechanisms 150 press the belt 140 inward from the outer side of the belt 140. By contrast, in the joining apparatus 100A according to the modified example, the pressing mechanisms 150 press the belt 140 outward from the inner side of the belt 140, as shown in FIG. 7. To be more specific, as seen in the axial direction of the anvil roller 120, the pressing mechanisms 150 press the belt 140 in respective directions of moving away from the imaginary line L.

In FIG. 7, the first and second pressing mechanisms 150A and 150B are provided. Alternatively, for example, only one of the first and second pressing mechanisms 150A and 1503 may be provided. In this case, it is particularly preferable to provide the second pressing mechanism 150B with which the belt 140 is more likely to be kept tensioned. It is however within the scope of the invention to provide only the first pressing mechanism 150B.

Further Embodiments

As described above, the details of several embodiments of the present invention have been exemplarily disclosed. It should not be understood that the description and drawings which constitute part of this disclosure limit the present invention. Based on this disclosure, those skilled in the art may easily come up with various alternative embodiments, examples and operation techniques.

For example, the following additional embodiments can be envisaged. Specifically, the absorbent article 1 has been described as including, in combination, the front waistline portion 10, the back waistline portion 20 and the crotch portion 30. The absorbent article 1 is not limited to this configuration, but may be formed entirely as a single unit. In this case, needless to say, a different method of manufacturing an absorbent article is employed.

The joining apparatus in the foregoing description has been described as for joining front and rear waistline portions. However, the joining apparatus is not limited to such use. For example, the joining apparatus can be used to join together any two or more layers, e.g., two separate webs, or two parts of the same web (e.g., folded web 7 after steps S4 in FIG. 2) etc. The webs and/or web parts are not necessarily front and rear waistline portions of wearing articles, but can be any two or more components of such wearing articles. For example, a waistline portion and an ear portion (for carrying a tape fastener) can be joined together by the joining apparatus in some embodiments.

In addition, the description has been provided for the joining apparatus 100 used in the manufacturing of pants-type disposable diapers. However, the joining apparatus 100 is not limited to such use. The joining apparatus 100 may be used to manufacture various products including open-type disposable diapers, sanitary napkins, panty liners, disposable gowns for medical use and disposable wearing articles for sports, for example.

Further, the belt 140 has been described as the connector. However, the connector is not limited to the belt 140. The connecter may be any tensionable connector, e.g., a general chain. In this case, a sprocket or the like to engage with the chain is employed for each of the anvil-side pulley 123 and the motor-side pulley 133.

Furthermore, the pressing mechanisms 150 have been described as constantly pressing the belt 140 in the respective cross directions DI. However, the pressing mechanisms 150 are not limited to such a configuration.

Also, the moving portions 152 have been described as constantly biasing the respective rotating portions 151 in the respective cross directions DI. However, the moving portions 152 are not limited to such a configuration.

The rotating portions 151 have been described as being moved (biased) in the respective cross directions DI. However, the movements of the rotating portions 151 are not limited to such a configuration. For example, the moving portions 152 may be fixed, and the rotating portions 151 are biased, in a rotational movement around the moving portions 152, against the belt 140. Alternatively, the rotating portions 151 may be biased both in the respective cross directions DI (by the moving portions 152) and in the rotational movement around the moving portions 152.

As described above, the present invention naturally includes various embodiments which are not described herein. Accordingly, the technical scope of the present invention should be determined only by the matters to define the invention in the scope of claims regarded as appropriate based on the description.

The entire content of Japanese Patent Applications 2009-048436 (filed on Mar. 2, 2009) and 2010-042135 (filed on Feb. 26, 2010) are incorporated herein by reference.

INDUSTRIAL APPLICABILITY

Therefore, according to the present invention, since it is possible to provide a joining apparatus and a method of manufacturing an absorbent article which are capable of achieving a more uniform joining in predetermined regions thereof, where joint portions of a front waistline portion and a back waistline portion are to be formed, and of reliably preventing a connector such as a belt from running off an anvil roller or a motor, in a case where the anvil roller and the motor are connected to each other via the connector, it is useful in manufacturing technology for absorbent articles.

REFERENCE SIGNS LIST 1 absorbent article
2 top sheet 3 back sheet
4 absorber
5 waterproof sheet
6 gather
6A waist gather
6B leg gather
7, 7A, 7B web
10 front waistline portion
10A side edge
20 back waistline portion
20A side edge
30 crotch portion
40 leg-surrounding openings
50 joint portion
50A predetermined region
60 waist openings
100, 100A joining apparatus
110 ultrasonic vibrating device
111 ultrasonic vibrator
112 booster
113 ultrasonic horn
114 pressurizing arm
120 anvil roller
121 anvil main body
122 protrusion
123 anvil-side pulley
130 motor
131 motor main body
132 rotational shaft
133 motor-side pulley
140 belt (connector)
150 pressing mechanism
150A first pressing mechanism
150B second pressing mechanism
151 rotating portion
152 moving portion
153 arm
160 guide roller
160A first guide roller
160B second guide roller

The invention claimed is:

1. A joining apparatus for joining two or more layers, the joining apparatus comprising:
    an ultrasonic vibrating device configured to apply ultrasonic vibration to a predetermined region where the layers are to be joined;
    an anvil roller facing the ultrasonic vibrating device, and including a protrusion configured to press the predetermined region of the layers against the ultrasonic vibrating device;
    a motor configured to rotate the anvil roller;
    a connector configured to connect the anvil roller and the motor and to be driven by the motor; and
    a pressing mechanism configured to press the connector in a direction transverse to a driving direction of the connector.

2. The joining apparatus according to claim 1, wherein the pressing mechanism includes:
    a rotating portion configured to abut on the connector and to be rotated in conjunction with the connector; and
    a moving portion configured to move the rotating portion in the transverse direction.

3. The joining apparatus according to claim 1, wherein the pressing mechanism is arranged in a region where the connector moves from the motor to the anvil roller in the driving direction.

4. The joining apparatus according to claim 1, wherein the pressing mechanism is arranged in a region where the connector moves from the anvil roller to the motor in the driving direction.

5. The joining apparatus according to claim 1, wherein the pressing mechanism is configured to press, as seen in an axial direction of the anvil roller, the connector toward an imaginary line connecting a center of a rotational shaft of the anvil roller and a center of a rotational shaft of the motor.

6. The joining apparatus according to claim 1, wherein the pressing mechanism constantly presses the connector.

7. A method of manufacturing an absorbent article having at least a front waistline portion and a back waistline portion, the method comprising the step of
    causing a joining apparatus to join a continuum of the front waistline portions and a continuum of the back waistline portions in a predetermined region, where a joint portion of each of the front waistline portions and each of the back waistline portions is to be formed, after the continuum of the front waistline portions and the continuum of the back waistline portions continuously fed are superimposed, wherein
    the joining apparatus includes:
    an ultrasonic vibrating device configured to apply ultrasonic vibration to the predetermined region;
    an anvil roller facing the ultrasonic vibrating device with the superimposed continua of the front waistline portions and the back waistline portions interposed therebetween, and including a protrusion configured to press the continua in the predetermined region between the anvil roller and the ultrasonic vibrating device;
    a motor configured to rotate the anvil roller;
    a connector configured to connect the anvil roller and the motor and to be driven by the motor; and
    a pressing mechanism configured to press the connector in a cross direction perpendicular to a driving direction of the connector.

* * * * *